United States Patent
Huang

(10) Patent No.: US 8,116,837 B2
(45) Date of Patent: Feb. 14, 2012

(54) SYSTEM FOR ADJUSTING POWER EMPLOYED BY A MEDICAL DEVICE

(75) Inventor: Johnnie W. Huang, Hillsborough, CA (US)

(73) Assignee: Draeger Medical Systems, Inc., Andover, MA (US)

(*) Notice: Subject to any disclaimer, the term of this patent is extended or adjusted under 35 U.S.C. 154(b) by 1620 days.

(21) Appl. No.: 11/482,509

(22) Filed: Jul. 7, 2006

(65) Prior Publication Data
US 2007/0038049 A1 Feb. 15, 2007

Related U.S. Application Data

(60) Provisional application No. 60/697,615, filed on Jul. 8, 2005.

(51) Int. Cl.
*A61B 5/1455* (2006.01)
(52) U.S. Cl. .......................... 600/310; 600/322
(58) Field of Classification Search ........... 600/309–344
See application file for complete search history.

(56) References Cited

U.S. PATENT DOCUMENTS

| | | |
|---|---|---|
| 4,859,057 A | 8/1989 | Taylor et al. |
| 4,892,101 A | 1/1990 | Cheung et al. |
| 5,069,214 A | 12/1991 | Samaras et al. |
| 5,746,697 A | 5/1998 | Swedlow et al. |
| 5,924,979 A | 7/1999 | Swedlow et al. |
| 6,863,652 B2 | 3/2005 | Huang et al. |

FOREIGN PATENT DOCUMENTS

| | | |
|---|---|---|
| EP | 0872210 A1 | 10/1998 |
| WO | WO03003914 A1 | 1/2003 |
| WO | WO03092490 A2 | 11/2003 |

OTHER PUBLICATIONS

European Search Report dated Feb. 29, 2008, Application No. EP06253582.

*Primary Examiner* — Eric Winakur
*Assistant Examiner* — Marjan Fardanesh
(74) *Attorney, Agent, or Firm* — Jack Schwartz & Associates, PLLC

(57) ABSTRACT

A system for adjusting power employed by a medical device incorporating light emitting devices and being used for measuring patient medical parameters, includes a plurality of light emitting devices. A power unit is coupled to the light emitting devices and powers the light emitting devices responsive to respective control signals which determine power to be applied to the light emitting devices. A control unit for provides the control signals and is coupled to the power unit. The control signals intermittently turn off at least one of the plurality of light emitting devices in a power save mode in response to a determination that a patient medical parameter value measured by the medical device, using an active light emitting device of the plurality of light emitting devices, is at a safe level.

12 Claims, 3 Drawing Sheets

SYSTEM FOR ADJUSTING POWER EMPLOYED BY A MEDICAL DEVICE

CROSS-REFERENCED TO RELATED APPLICATIONS

This is a non-provisional application of U.S. Provisional Application Ser. No. 60/697,615 filed Jul. 8, 2005.

FIELD OF THE INVENTION

The present invention relates to power conservation in portable medical devices, and in particular to power conservation in portable medical devices which use light emitting devices.

BACKGROUND OF THE INVENTION

Recent trends in miniaturization of medical devices, in particular the design and implementation of patient monitors as portable units, have created the need to maximize power conservation in order to reduce the required size of the attached battery. Standalone pulse oximetry systems have generally not attempted to conserve power because either the continuous AC power is available or a sizable battery is attached. Present monitoring needs, however, demand smaller profile, higher computational capacity for advanced algorithmic processing, integration with monitoring capability for other medical parameters, and also portability. In general, therefore, it is desirable to minimize power consumption. Power conservation in the pulse oximetry system, in particular, can yield additional running time for other medical parameter monitors in a multi-parameter patient monitor running on batteries.

In a typical pulse oximetry system, as much as 50% of power is used for driving the light emitting diodes (LEDs). Therefore, minimizing the power consumption of the LEDs enhances the lifetime of a battery after a full charge. In addition, advances in accurate calculation of blood oxygen level and pulse rate by pulse oximetry systems are due to the development of sophisticated algorithms and the integration of high capacity data processors capable of performing these algorithms into pulse oximetry systems. Such high capacity processors can also consume a significant amount of power. Minimizing the power consumption of the data processor can also enhance the lifetime of a battery after a full charge. A system according to invention principles addresses these needs and associated problems.

BRIEF SUMMARY OF THE INVENTION

In accordance with principles of the present invention, a system for adjusting power employed by a medical device incorporating light emitting devices and being used for measuring patient medical parameters, includes a plurality of light emitting devices. A power unit is coupled to the light emitting devices and powers the light emitting devices responsive to respective control signals which determine power to be applied to the light emitting devices. A control unit provides the control signals and is coupled to the power unit. The control signals intermittently turn off at least one of the plurality of light emitting devices in a power save mode in response to a determination that a patient medical parameter value measured by the medical device, using an active light emitting device of the plurality of light emitting devices, is at a safe level.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, medical device system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

Figure 1:
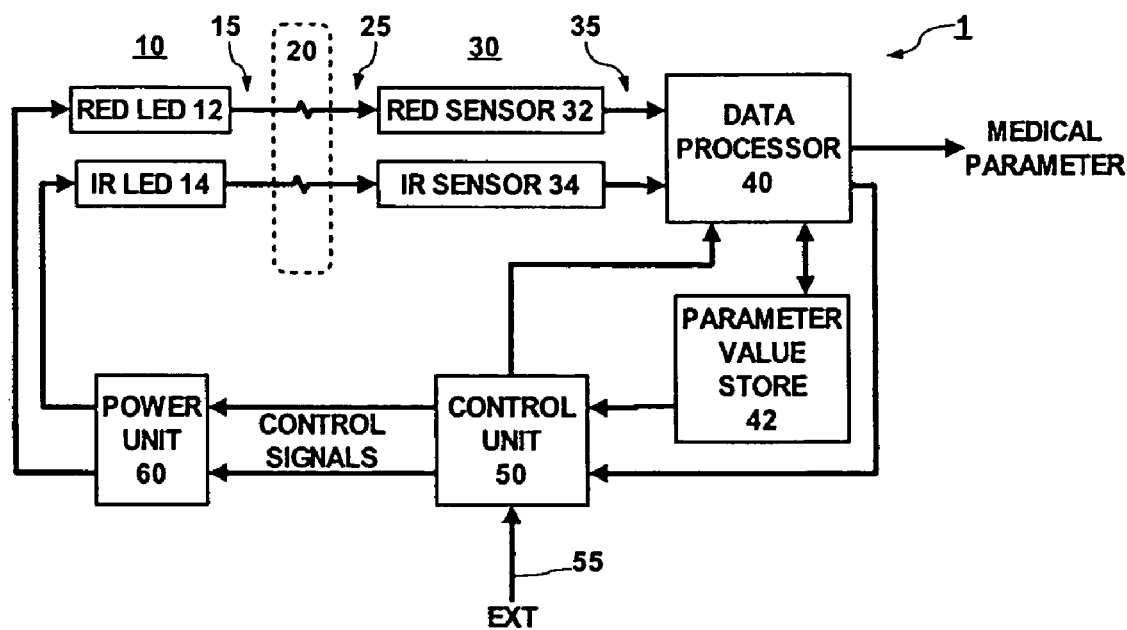
FIG. 1 is a block diagram of a system according to principles of the present invention.

FIG. 1 illustrates a portion of a medical device, incorporating light emitting devices, used to measure patient medical parameters. FIG. 1 is a block diagram of a system 1 employed by such a medical device for adjusting power employed by the medical device. In system 1, a plurality 10 of light emitting devices 12, 14 produce respective light signals 15. The light signals 15 are passed through, or reflected off of, biological tissue 20. The resulting respective light signals 25, modified by passing through or being reflected off of the biological tissue 20, are received by a corresponding plurality 30 of light sensor devices 32, 34. The plurality 30 of light sensor devices 32, 34 convert the received light signals 25 into corresponding electrical signals 35. Respective output terminals of the plurality 30 of light sensor devices 32, 34 are coupled to corresponding input terminals of a data processor 40. A signal output terminal of the data processor 40 generates a medical parameter, and data processor 40 provides a further signal coupled to an input terminal of a control unit 50. A control output terminal of the data processor 40 is coupled to an input terminal of a parameter value store 42. An output terminal of the parameter value store 42 is coupled to a second input terminal of the control unit 50. Respective output terminals of the control unit 50 generates control signals, and are coupled to corresponding control input terminals of a power unit 60. Respective output terminals of the power unit 60 are coupled to corresponding input terminals of the plurality 10 of light emitting devices 12, 14. A control output terminal of the control unit 50 is coupled to a control input terminal of the data processor 40. An input terminal 55 is coupled to a source (not shown) of a control signal. The input terminal 55 is coupled to a control input terminal of the control unit 50.

In operation, the power unit 60 powers the plurality 10 of light emitting devices 12, 14, responsive to the respective control signals. The control signals determine the power applied to the plurality 10 of light emitting devices 12, 14. The control unit 50, coupled to the power unit 60, provides the control signals. The control signals condition the power unit 60 to intermittently turn off at least one of the plurality 10 of light emitting devices 12, 14 in a power save mode. The control unit 50 initiates the power save mode in response to a determination that a patient medical parameter value measured by the medical device using an active light emitting device of the plurality of light emitting devices, is at a safe level.

For example, the system 1 may be implemented in a pulse oximeter medical device. A pulse oximeter produces successive blood oxygen saturation (e.g. $SpO_2$) and/or pulse rate (e.g. PLS) readings as the patient medical parameter values. In a pulse oximeter, the light emitting devices 10 are typically light emitting diodes (LEDs). The first LED 12 emits red light and the second LED 14 emits infrared (IR) light. They are typically time multiplexed to produce light signals 15 one at a time to produce a single $SpO_2$ and/or pulse rate reading. Respective signals 35 from the red 12 and IR 14 light sensors 32, 34 are read by the data processor 40 when the corresponding LED is on. The data processor 40 then processes those signals to calculate an $SpO_2$ and/or the pulse rate reading. Intermediate components are also typically calculated. For example, ac and dc components of the respective red and IR LED signals 35 are calculated and stored, and those components used to calculate the $SpO_2$ and/or pulse rate medical parameter.

In a pulse oximeter medical device, the system 1 enters a power save mode (described in more detail below) when a patient medical parameter value is at a safe level. The patient medical parameter value may be one measured by the medical device itself. For example, the patient medical parameter value may be the blood oxygen saturation representative value. The control unit 50 determines that the patient medical parameter value (e.g. the blood oxygen saturation representative value) is at a safe level when it is above a predetermined threshold, for example. The patient medical parameter value may also be the pulse rate. The control unit 50 determines that the patient medical parameter value (e.g. the pulse rate) is at a safe level when it is within a predetermined range.

Similarly, the patient medical parameter value may indicate a change in the blood oxygen saturation representative value or a change in the pulse rate. The control unit 50 also determines that the patient medical parameter value (e.g. the change in blood oxygen saturation representative value or pulse rate) is at a safe level when it is less than a predetermined value. The patient medical parameter value may also be a rate-of-change of the blood oxygen saturation representative parameter or pulse rate. The control unit 50 further determines that the patient medical parameter value (e.g. rate-of-change of the blood oxygen saturation value or rate-of-change of the pulse rate) is at a safe level when it is within a predetermined range.

It is also possible for the patient medical parameter value which controls entry to the power save mode to be provided from an external source, such as a separate patient monitoring device measuring other patient medical parameters. The patient medical parameter value may also be entered manually. An output terminal of such an external patient monitoring device (not shown) and/or manual input device (also not shown) may be coupled to the control unit 50 via the external terminal 55. The patient medical parameter value, in such a case, may be at least one of: patient temperature; arterial blood pressure; a hematocrit level; and/or a cardiac index. One or more of the patient medical parameter values described above, and/or any other similar patient medical parameter value, may be used by the control unit 50 to determine if the patient medical parameter value is at a safe level.

Figure 2:
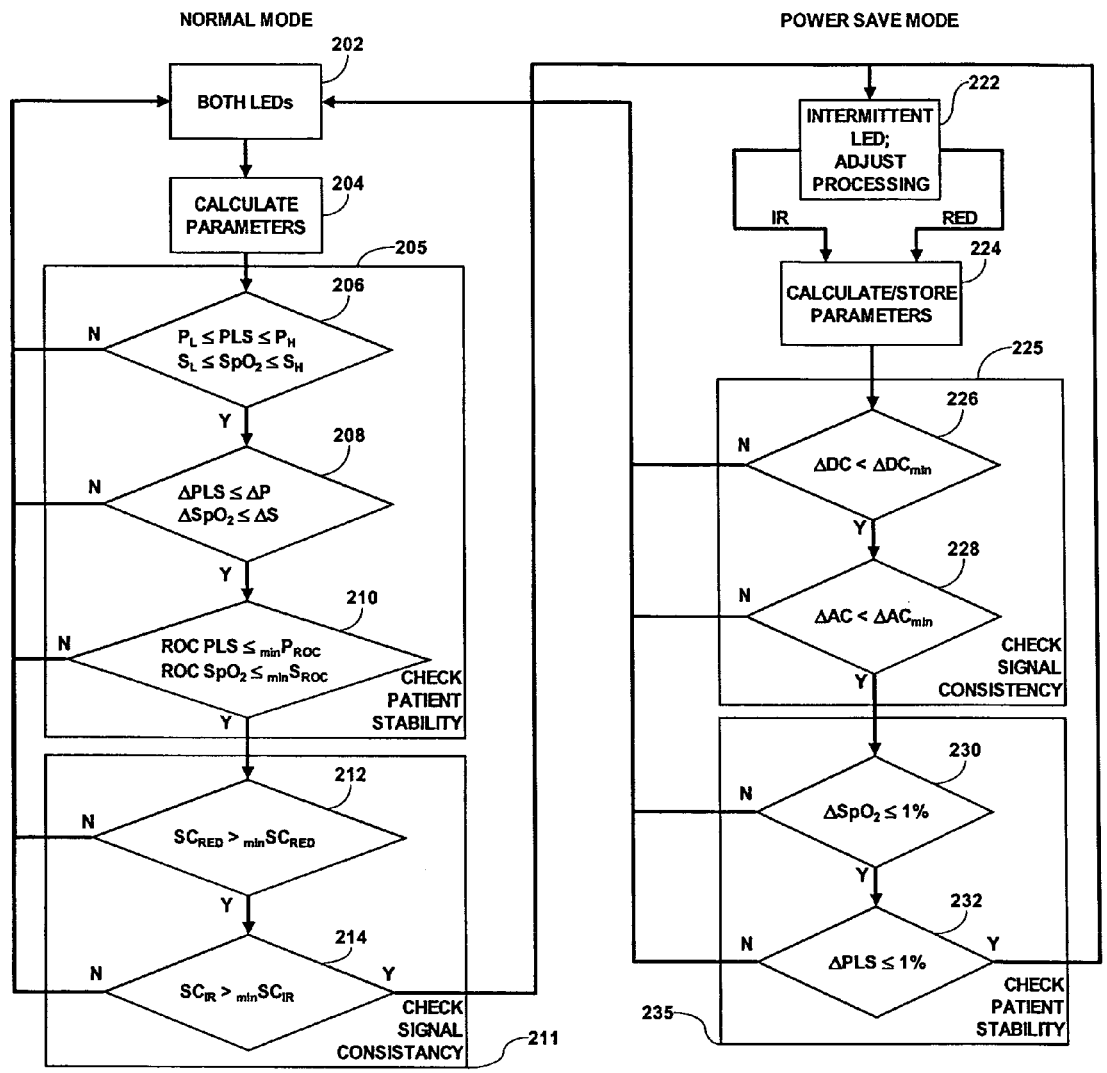
FIG. 2 is a flow chart illustrating the process of entering and terminating a power save mode in the system of FIG. 1 according to the present invention.

In the illustrated pulse oximeter embodiment, the patient medical parameter value is determined to be at a safe level when the $SpO_2$ and pulse rate parameters are stable and within a predetermined range of acceptable values. This is illustrated in FIG. 2 which illustrates the process of entering and terminating the power save mode in the system illustrated in FIG. 1. For example, in an adult, the $SpO_2$ reading should be between 90% and 100% and the pulse rate should be between 50 and 100 beats per minute (bpm). Stability is determined by the change and the rate-of-change in the $SpO_2$ and pulse rate values being less than a relatively low threshold. The acceptable range of $SpO_2$ and pulse rate values, and threshold levels for the change in these values may be adjusted by a user. The control unit 50 receives the $SpO_2$ and pulse rate values from the data processor 40, and calculates the change in those values and the rate-of-change of those values.

More specifically, in the illustrated embodiment, both LEDs 12 and 14 are enabled in step 202. In step 204 values for $SpO_2$ and pulse rate (PLS) medical parameters are calculated by the data processor 40 based on the signals 35 representing the received light from the LEDs 12, 14. In block 205, patient stability is determined. In step 206 the pulse rate value PLS is compared to low and high thresholds $P_L$ and $P_H$, respectively, and the $SpO_2$ value is compared to low and high thresholds, $S_L$ and $S_H$, respectively. If the PLS value is between $P_L$ and $P_H$ and the $SpO_2$ value is between $S_L$ and $S_H$, then step 208 is performed, otherwise, the medical device remains in normal mode and operation returns to step 202. In step 208 the change in the PLS value ($\Delta PLS$) is compared to a thresholds $\Delta P$, and the change in the $SpO_2$ value ($\Delta SpO_2$) is compared to a threshold $\Delta S$. If the $\Delta PLS$ value is less than the $\Delta P$ threshold, and the $\Delta SpO_2$ value is less than the $\Delta S$ threshold, then step 210 is performed, otherwise, the medical device remains in normal mode and operation returns to step 202. In step 210 the rate-of-change of the PLS value (ROC PLS) is compared to a thresholds $_{min}P_{ROC}$, and the rate-of-change in the $SpO_2$ value (ROC $SpO_2$) is compared to a threshold $_{min}S_{ROC}$. If the ROC $SpO_2$ value is less than the $_{min}S_{ROC}$ threshold, and the ROC PLS value is less than the $_{min}P_{ROC}$ threshold, then step 210 is performed, otherwise, the medical device remains in normal mode and operation returns to step 202.

In addition to checking the medical parameter to determine if the patient is safe and stable, it is also possible to check other signal parameters to determine whether the patient and the system are in condition to operate in a power save mode. In FIG. 2, a check is made on the consistency of the signals 35, representing the light received from the plurality 10 of LEDs 12 and 14. Signal consistency may be represented by the signal-to-noise ratio of the received signal, by drift of signal components, such as an ac and/or dc component, or any other similar measure of signal consistency.

In block 211, signal consistency is determined. In step 212 the signal consistency of the signal 35 ($SC_{RED}$) representing the light received from the red LED 12 is compared to a threshold $_{min}SC_{RED}$. If the signal consistency of the red signal $SC_{RED}$ is greater than the threshold $_{min}SC_{RED}$, then step 214 is performed, otherwise, the medical device remains in normal mode and operation returns to step 202. Similarly, in step 212 the signal consistency of the signal 35 ($SC_{IR}$) representing the light received from the IR LED 14 is compared to a threshold $_{min}SC_{IR}$. If the signal consistency of the IR signal $SC_{IR}$ is greater than the threshold $_{min}SC_{IR}$, then the patient is considered to be stable and the signals consistent. In this case, the system 1 (FIG. 1) enters the power save mode and step 222 is performed, otherwise, the medical device remains in normal mode and operation returns to step 202.

In one embodiment, the control unit 50 (FIG. 1) provides control signals to the power unit 60 conditioning it to intermittently turn off at least first and second different LEDs 12, 14 of the plurality 10 of LEDs 12, 14 in the power save mode. Referring again to FIG. 2, in step 222, one of the plurality 10 of LEDs is turned off. In this mode, when one LED (e.g. 12) is turned off, the other LED (e.g. 14) remains active. Prior to turning off an LED (e.g. 12), parameter values obtained using the active LED are stored in the parameter value store 42. In step 224, the parameter values for the LED to be turned off are stored, and a reading is taken using the other, active, LED.

More specifically, in the illustrated embodiment, parameter values resulting from e.g. intermediate calculations made by the data processor 40 (FIG. 1) related to the IR LED (e.g. 14) are stored in the parameter value store 42. When that LED (e.g. 14) is turned off, the stored parameter values are retrieved from the parameter value store 42 and used together with the parameter values obtained using the active LED (e.g. the IR LED 14) to calculate the medical parameter, e.g. $SpO_2$ and/or pulse rate. The calculation of the medical parameter, i.e. $SpO_2$ and/or pulse rate, are performed in step 224. In addition, the control unit 50 retrieves the stored parameter value from the parameter value store 42, and uses the stored parameter values obtained using the previously active LED (e.g. 14) together with a parameter values obtained using the active LED (e.g. 12) to determine that the patient medical parameter value measured by the medical device is remaining at a safe level while in the power save mode.

As described above, in the illustrated embodiment, the patient medical parameter value is considered at a safe level if the patient remains stable and the signal remains consistent. Block 225 checks signal consistency. In step 226 the change in the dc level $\Delta DC$ of the active LED (e.g. 14) signal 35 is compared to a threshold $\Delta DC_{min}$. If $\Delta DC$ is less than the threshold $\Delta DC_{min}$ then step 228 is activated. Otherwise, it is determined that the signal is not consistent and the power save mode is terminated by returning to step 202 where both LEDs are activated. In step 228 the change in the ac level $\Delta AC$ of the active LED (e.g. 14) signal 35 is compared to a threshold $\Delta AC_{min}$. If $\Delta AC$ is less than the threshold $\Delta AC_{min}$ then step 230 is activated. Otherwise, it is determined that the signal is not consistent and the power save mode is terminated by returning to step 202 where both LEDs are activated.

In block 235, patient stability is checked. In step 230, the change in the $SpO_2$ parameter $\Delta SpO_2$ is compared to a threshold. In the illustrated embodiment, the threshold is 1%. If the change in the $SpO_2$ parameter $\Delta SpO_2$ is less than 1%, then step 232 is activated. Otherwise, it is determined that the patient is not stable and the power save mode is terminated by returning to step 202 where both LEDs are activated. In step 232, the change in the pulse rate parameter $\Delta PLS$ is compared to a threshold. In the illustrated embodiment, the threshold is also 1%. If the change in the PLS parameter APLS is less than 1%, then it is determined that the patient remains stable and the signal remains consistent. In this case, the system remains in the power save mode by returning to step 222. Otherwise, it is determined that the patient is not stable and the power save mode is terminated by returning to step 202 where both LEDs are activated.

One skilled in the art understands that turning off one LED (e.g. 14) and using stored parameters representing the signals received when that LED was last active to calculate the medical parameter, i.e. $SpO_2$ and/or pulse rate, some inaccuracy may enter into the medical parameter value. However, because the power save mode is entered when the patient is stable, meaning that the medical parameter $SpO_2$ and/or pulse rate is relatively unchanging, the inaccuracy is relatively small, and is a reasonable trade off compared to the power savings entailed by turning off one LED.

In the embodiment illustrated in FIG. 2, the system remains in the power save mode for as long as the patient remains stable and the signals remain consistent. Alternatively, at some point in time, which may be a predetermined time duration, a predetermined number of heart beats, a predetermined number of readings of the medical parameter measured by the medical device, or a time period determined in any other similar manner, the system automatically terminates the power save mode, and returns to the normal mode. This may be done to reset the stored parameters for the LED which was turned off. The predetermined time duration may be user configurable Also as described above, an external patient monitor may supply patient medical parameters to the control unit 50 via the external terminal 55. The control unit 50 monitors the patient medical parameters from the external patient monitor, i.e. the medical parameters that are measured without using at least one of the plurality 10 of light emitting devices 12, 14. In response to a determination that the externally monitored patient medical parameter value is outside a predetermined range, the control unit 50 terminates the power save mode and turns on the light emitting device (e.g. 14) of the plurality of light emitting devices which was previously turned off.

Figure 3:
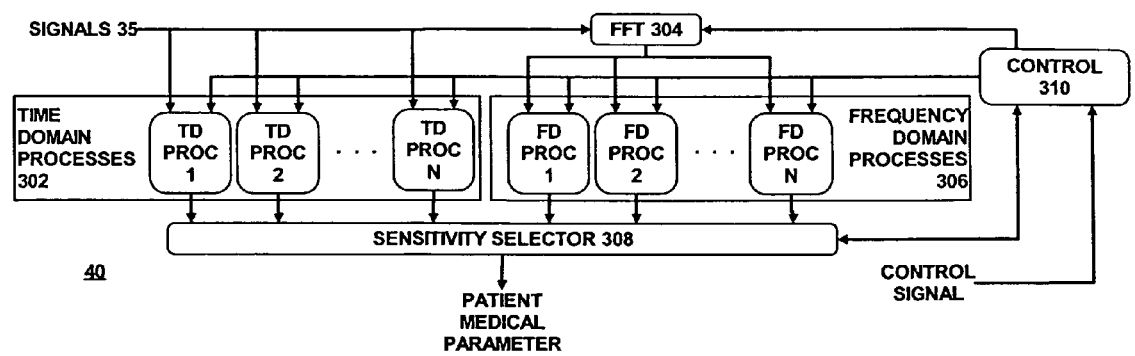
FIG. 3 is a block diagram illustrating a portion of the processing which is performed in a data processor according to the present invention.

As described above, power is also employed by the data processor 40 (FIG. 1) in performing the processing necessary to derive the patient medical parameter, e.g. $SpO_2$ and/or pulse rate, from the signals 35 representing the received light signals 25. FIG. 3 is a block diagram illustrating a portion of the processing which is performed in the data processor 40 according to the present invention. In FIG. 3, the light representative signals 35 are coupled to respective signal input terminals of time domain processes 302 and to a signal input terminal of an FFT process 304. An output terminal of the FFT process 304 is coupled to respective signal input terminals of frequency domain processes 306.

More specifically, in the illustrated embodiment, a plurality of N time domain processes, TD PROC 1, TD PROC 2, . . . TD PROC N, are illustrated. The light representative signals 35 are coupled to respective signal input terminals of the plurality 302 of time domain processes, TD PROC 1, TD PROC 2, . . . TD PROC N. Similarly, a plurality of N frequency domain processes, FD PROC 1, FD PROC 2, . . . FD PROC N, are illustrated. The output terminal of the FFT process 304 is coupled to respective signal input terminals of the plurality 306 of frequency domain processes 306, FD PROC 1, FD PROC 2, . . . FD PROC N.

The control signal from the control unit 50 (FIG. 1) to the data processor 40 is coupled to an input terminal of a control process 310. Respective output terminals of the control process 310 are coupled to corresponding control input terminals of the plurality 302 of time domain processes, TD PROC 1, TD PROC 2, . . . TD PROC N, and the plurality 306 of frequency domain processes, FD PROC 1, FD PROC 2, . . . FD PROC N. Respective control output terminals of the controller 310 are also coupled to corresponding control input terminals of the FFT process 304 and the sensitivity selector 308.

In operation, the data processor 40 employs a plurality of different processing functions (TD PROC 1, TD PROC 2, ... TD PROC N; FD PROC 1, FD PROC 2, ... FD PROC N) for processing the data in the signals 35 (FIG. 1) derived using the plurality 10 of light emitting devices 12, 14 in determining the patient medical parameter value, e.g. SpO$_2$, pulse rate, measured by the medical device. A subset 302 of the plurality of processing functions operate in the time domain. Another subset 304 of the plurality of processing functions operate in the frequency domain. The control unit 50 provides a control signal to the control process 310 in the data processor 40 for turning off at least one processing function of the plurality of processing functions (TD PROC 1, TD PROC 2, ... TD PROC N; FD PROC 1, FD PROC 2, ... FD PROC N) in the power save mode in response to a predetermined function disablement procedure, described in more detail below. As described above, the power save mode may be initiated in response to a determination that the patient medical parameter (e.g. SpO$_2$, pulse rate), measured by the medical device using the active light emitting device (e.g. 14) of the plurality 10 of light emitting devices 12, 14, is at a safe level. More specifically, in the illustrated embodiment, the power save mode is initiated in step 222 of FIG. 2.

In the illustrated embodiment, the predetermined function disablement procedure turns off at least one processing function (TD PROC 1, TD PROC 2, ... TD PROC N; FD PROC 1, FD PROC 2, ... FD PROC N) in response to a sensitivity determination. The sensitivity determination is used to turn off the function (TD PROC 1, TD PROC 2, ... TD PROC N; FD PROC 1, FD PROC 2, ... FD PROC N) having least effect in the determination of the patient medical parameter value (e.g. SpO$_2$, pulse rate) measured by the medical device. In an alternative embodiment, the control unit 50 provides control signals 40 to the control process 310 for progressively turning off processing functions of the plurality of processing functions (TD PROC 1, TD PROC 2, ... TD PROC N; FD PROC 1, FD PROC 2, ... FD PROC N) in the power save mode in response to the sensitivity determinations.

In the illustrated embodiment, the sensitivity selector 310 operates as probability-based classifier. Such a selector 310 classifies the results from the plurality of processing functions (TD PROC 1, TD PROC 2, ... TD PROC N; FD PROC 1, FD PROC 2, ... FD PROC N), termed features, based on the calculated probability, termed sensitivity, of their being accurate estimates of the patient medical parameter, e.g. SpO$_2$, pulse rate. With such a selector, the number of features (TD PROC 1, TD PROC 2, ... TD PROC N; FD PROC 1, FD PROC 2, ... FD PROC N) used for the classifier computation may be reduced without compromising performance. The decision to select a particular feature (TD PROC 1, TD PROC 2, ... TD PROC N; FD PROC 1, FD PROC 2, ... FD PROC N) to turn off is based on the sensitivity of that feature. During a typical computing iteration, multiple possible outcomes (e.g. SpO$_2$ readings and/or pulse rate frequencies) are considered concurrently by the feature processes (TD PROC 1, TD PROC 2, ... TD PROC N; FD PROC 1, FD PROC 2, ... FD PROC N). A feature process (TD PROC 1, TD PROC 2, ... TD PROC N; FD PROC 1, FD PROC 2, ... FD PROC N) assigns a probability value to the possible outcomes. The power of classification is computed for an individual feature process (TD PROC 1, TD PROC 2, ... TD PROC N; FD PROC 1, FD PROC 2, ... FD PROC N) to assess its sensitivity level S. For example, for a feature process (TD PROC 1, TD PROC 2, ... TD PROC N; FD PROC 1, FD PROC 2, ... FD PROC N) with n possible outcomes, the sensitivity S is computed by comparing the respective probabilities P$_n$ of an outcome to the probability of the last reported outcome P' where:

$$S = \frac{1}{N}\sum_{n=1}^{N}(P' - P_n)$$ (Equ 1)

The process (TD PROC 1, TD PROC 2, ... TD PROC N; FD PROC 1, FD PROC 2, ... FD PROC N) with the lowest sensitivity level S is turned off and consequently not processed by the sensitivity selector 308. In an alternate embodiment, processes (TD PROC 1, TD PROC 2, ... TD PROC N; FD PROC 1, FD PROC 2, ... FD PROC N) having the lowest sensitivity level S are progressively turned off. With fewer processes operating, power consumption by the data processor 40 is reduced.

It is further possible to control the FFT process 304 to reduce the processing required, and therefore, the power consumption. One skilled in the art understands that an FFT process transforms a set of time domain input samples, representing the respective signals 35 from the plurality 10 of light emitting devices 12, 14, into a corresponding set of frequency domain output samples. The control unit 50 (FIG. 1) provides a control signal to the control process 310 in the data processor 40 which conditions the FFT process 304 to reduce the processing required to produce the frequency domain samples in the power save mode. Specifically, the number of samples in the input and output sample set, and the rate at which conversion cycles are made may be controlled. In the power save mode, the number of samples in the set of time domain samples (and corresponding frequency domain output samples) is reduced and/or the rate at which successive sets of time domain input samples are transformed into corresponding sets of frequency domain samples is reduced. Less power is consumed when fewer samples are transformed, and when the rate of conversion cycles is reduced.

In the illustrated embodiment, the processing blocks in FIG. 3 (e.g. TD PROC 1, TD PROC 2, ... TD PROC N; FD PROC 1, FD PROC 2, ... FD PROC N, 304, 308, 310) represent executable procedures which may be executed by the data processor 40. One skilled in the art understands that these processing blocks may be implemented in hardware, firmware, software or any combination of the three.

It is also possible that a medical device, such as a pulse oximeter medical device, may be one component in a multifunction patient monitor device. For example, a multifunction patient monitor device may include an ECG monitor, blood pressure monitor, temperature monitor, ventilation monitor, etc. in addition to the pulse oximeter monitor providing SpO$_2$ and pulse rate medical parameters. In such a multifunction medical device, it is possible to provide further power savings by turning off operation of the pulse oximeter functions completely. More specifically, in the illustrated embodiment, the pulse oximeter system uses the plurality 10 (FIG. 1) of light emitting devices 12, 14 to derive the SpO$_2$ and pulse rate patient medical parameters. However, the other medical devices in the multifunction monitor derive patient medical parameters (i.e. ECG lead signals, blood pressure, temperature, ventilation parameters, etc.) without using the plurality 10 of light emitting devices 12, 14.

In such a monitor, the control unit 50 (FIG. 1) may provide a control signal coupled to the power unit 60 for turning off the light emitting device in a power save mode for a predetermined time duration. The control unit 50 may further provide a control signal for turning off processing of data occurring in deriving the patient medical parameter (e.g. SpO$_2$, pulse rate) using the light emitting device. The control unit 50

(FIG. 1) may instead provide a control signal turning off operation of the medical device functions which are unused in deriving the patient medical parameter (e.g. SpO$_2$, pulse rate) that is measured without using the light emitting devices 12, 14 in response to a determination that the patient medical parameter value measured by the medical device using an active light emitting device (e.g. 14) of the plurality 10 of light emitting devices 12, 14 (e.g. SpO$_2$, pulse rate), is at a safe level. The control unit 50 then monitors a patient medical parameter that is measured without using the light emitting devices 12, 14 (e.g. EKG, temperature, ventilation parameters, etc.) and in response to a determination that the monitored patient medical parameter value is outside of a predetermined range, terminates the power save mode and turns on the light emitting devices 12, 14 and the processing of data. In this manner, the power consumed by the pulse oximeter monitor may be eliminated or substantially reduced.

What is claimed is:

1. A system for adjusting power employed by a medical device incorporating light emitting devices and being used for measuring patient medical parameters, comprising:
    a plurality of light emitting devices;
    a power unit coupled to said light emitting devices for powering said light emitting devices responsive to respective control signals for determining power applied to said light emitting devices; and
    a control unit for providing said control signals and being coupled to the power unit, said control signals intermittently turning off at least one of said plurality of light emitting devices in a power save mode in response to a determination that a patient medical parameter value measured by said medical device, using an active light emitting device of said plurality of light emitting devices, remains at a safe level,
    wherein, in said power save mode, at least one of said plurality of light emitting devices is in an active state.

2. The system according to claim 1, wherein said control unit determines said patient medical parameter value comprising a blood oxygen saturation representative value is at said safe level by being above a predetermined threshold.

3. The system according to claim 2, wherein said control unit determines said patient medical parameter value comprising a pulse rate is at said safe level by being within a predetermined range.

4. The system according to claim 1, wherein said patient medical parameter comprises at least one of:
    a blood oxygen saturation representative parameter;
    a change in a blood oxygen saturation representative parameter;
    a rate-of-change of a blood oxygen saturation representative parameter;
    a pulse rate;
    a change in pulse rate;
    patient temperature;
    arterial blood pressure;
    a hematocrit level; and
    a cardiac index.

5. A system for adjusting power employed by a medical device incorporating light emitting devices and being used for measuring patient medical parameters, comprising:
    a plurality of light emitting devices;
    a power unit coupled to said light emitting devices for powering said light emitting devices and responsive to respective control signals for determining power applied to said light emitting devices; and
    a control unit for providing said control signals and being coupled to the power unit, said control signals intermittently turning off at least first and second different light emitting devices of said plurality of light emitting devices in a power save mode in response to a determination that a patient medical parameter value measured by said medical device, using an active light emitting device of said plurality of light emitting devices, remains at a safe level; wherein:
    said medical device stores a parameter value obtained using an active first light emitting device prior to turning off said active first light emitting device; and, in said power save mode, at least one of said plurality of light emitting devices is in an active state.

6. The system according to claim 5, wherein said control unit uses said stored parameter value obtained using said first light emitting device together with a parameter value obtained using an active second light emitting device to determine said patient medical parameter value measured by said medical device is at a safe level.

7. The system according to claim 5, further comprising:
    a data processor employing a plurality of different processing functions for processing data derived using said plurality of light emitting devices in determining said patient medical parameter value measured by said medical device; wherein:
    said control unit provides a control signal for turning off at least one processing function of said plurality of processing functions in said power save mode in response to a sensitivity determination, said sensitivity determination being used to turn off a function having least effect in said determination of said patient medical parameter value measured by said medical device.

8. The system according to claim 7, wherein said control unit provides control signals for progressively turning off processing functions of said plurality of processing functions in said power save mode in response to sensitivity determinations.

9. The system according to claim 7, wherein
    a subset of the plurality of processing functions operates in the frequency domain;
    the system further comprises a fast Fourier transform (FFT) processing function, for transforming a set of time domain input samples, representing respective signals from said plurality of light emitting devices, into a corresponding set of frequency domain samples; and
    said control unit provides control signals for reducing the processing required to produce said frequency domain samples in said power save mode.

10. The system according to claim 9 wherein the number of samples in the set of time domain samples is reduced in said power save mode.

11. The system according to claim 9 wherein the rate at which successive sets of time domain samples are transformed into corresponding sets of frequency domain output samples is reduced in said power save mode.

12. The system according to claim 5, wherein
    said control unit provides a control signal for turning off said at least one of said plurality of light emitting devices in a power save mode for a user configurable predetermined time duration and monitors a patient medical parameter that is measured without using said at least one of said plurality of light emitting devices; and
    in response to a determination said monitored patient medical parameter value is outside a predetermined range, said control unit terminates said power save mode and turns on said at least one of said plurality of light emitting devices.

* * * * *